(12) United States Patent
Szul

(10) Patent No.: US 12,011,607 B2
(45) Date of Patent: Jun. 18, 2024

(54) ASSISTANT FOR GARMENT AND WEARABLE DEVICE FITTING

(71) Applicant: WEST AFFUM HOLDINGS DAC, Dublin (IE)

(72) Inventor: Krystyna Szul, Seattle, WA (US)

(73) Assignee: West Affum Holdings DAC, Dublin (IE)

( * ) Notice: Subject to any disclaimer, the term of this patent is extended or adjusted under 35 U.S.C. 154(b) by 53 days.

(21) Appl. No.: 17/163,099

(22) Filed: Jan. 29, 2021

(65) Prior Publication Data

US 2022/0054848 A1    Feb. 24, 2022

Related U.S. Application Data

(60) Provisional application No. 63/069,630, filed on Aug. 24, 2020.

(51) Int. Cl.
| | |
|---|---|
| *A61N 1/39* | (2006.01) |
| *A61N 1/04* | (2006.01) |
| *G06F 3/01* | (2006.01) |
| *G06F 3/14* | (2006.01) |

(52) U.S. Cl.
CPC ........... *A61N 1/3904* (2017.08); *A61N 1/046* (2013.01); *A61N 1/0484* (2013.01); *G06F 3/011* (2013.01); *G06F 3/14* (2013.01)

(58) Field of Classification Search
CPC .... A61N 1/046; A61N 1/0484; A61N 1/3904; G06F 3/011; G06F 3/14; G06F 3/147; G09G 2380/08
USPC .......................................................... 607/5
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |

(Continued)

FOREIGN PATENT DOCUMENTS

WO        9839061 A2    9/1998

OTHER PUBLICATIONS

Heartstart MRx and XL AED Algorithm—Application Note, Jul. 2001, Edition 2 Philips Healthcare, USA.

(Continued)

*Primary Examiner* — Carl H Layno
*Assistant Examiner* — Jane C Kalinock
(74) *Attorney, Agent, or Firm* — Polsinelli PC

(57) ABSTRACT

Augmented, virtual, and/or mixed reality applications in optimizing a fitting process and a fit of wearables, including wearable cardioverter defibrillators, to a wearer's body.

20 Claims, 7 Drawing Sheets

(56) References Cited

U.S. PATENT DOCUMENTS

| | | |
|---|---|---|
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2018/0242920 A1* | 8/2018 | Hresko ................. A61B 5/0006 |
| 2019/0385744 A1* | 12/2019 | Freeman ................ A61B 5/681 |
| 2021/0343017 A1* | 11/2021 | Jordan .................. G06T 7/0016 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

\* cited by examiner

SAMPLE COMPONENTS OF WEARABLE CARDIOVERTER DEFIBRILLATOR (WCD) SYSTEM

COMPONENTS OF EXTERNAL DEFIBRILLATOR

Sensing Electrode Placement

ASSISTANT FOR GARMENT AND WEARABLE DEVICE FITTING

CROSS-REFERENCE(S) TO RELATED APPLICATION(S)

This patent application claims the benefit of and priority to U.S. Provisional Patent Application Ser. No. 63/069,630, filed on Aug. 24, 2020, titled: "System and Method for AR/VR—Assisted Garment and Wearable Device Fitting and Maintenance," the disclosure of which is hereby incorporated by reference in its entirety for all purposes.

This patent application may be found to be related to U.S. Utility Patent Application Ser. No. 16/946,512, filed on Jun. 24, 2020, titled: "Wearable Cardioverter Defibrillator With AI-Based Features," incorporated herein by reference in its entirety for all purposes.

BACKGROUND

Obtaining physical health indicators or parameters requires use of hardware-based devices. Hardware devices, including monitoring and/or treatment devices can be, but are not limited to wearable devices such as a wearable defibrillator (WD) or a wearable cardioverter defibrillator (WCD) system, ECG monitor, heart rate monitor, blood pressure monitor, pulse oxygenation, glucose, temperature, transthoracic impedance, activity, posture, gait, other types of sensors, meters, and monitoring sub-systems, etc. Such devices can include adhesive pads or patches.

A wearable system that includes one or more of the above-mentioned devices can further include a means of attachment of the device to a wearer's body. The means of attachment can be a scaffold, a garment, a belt, an adhesive, or other type of attachment means intended to facilitate placement of wearable device elements about a wearer's body. Often, the means of attachment come in a one-size-fits-all, or at most, in predetermined sizes for an estimated population range, defaulting a wearer to his/her size range of typically small, medium, and/or large size. The challenge and predicament with one-size-fits-all and even seemingly customized small/medium/large sizes, is that they may not consider different body shapes or gender, contours, size, anatomy, physiology, age, any personal or clinical preferences, etc. Wearable systems can facilitate sensing, data acquisition, analysis, monitoring, therapy, and even aid prognostication. If the fit is not just right however, data may be skewed, noisy, or even not usable altogether.

Since WCDs, for example, are intended to be worn for an extended period for the purpose of monitoring physiological signals, and based on those signals, deciding whether to discharge energy to a patient's heart, an imprecise placement of sensing and/or therapy components may disadvantage the wearer/patient from the get-go. Additional factors such as wearer's discomfort may also impede wearability to the point where a patient may avoid wearing the device, which would defeat the purpose altogether.

Precise, comfortable securement of a wearable for an extended period, that also allows a wearer to engage in ambulatory activities, can be determinative of wear compliance, data quality and accuracy, and potentially also patient outcome. Furthermore, during the wear period, promptness of attention to issues related any discomfort or the wearable shifting out of place can affect patient satisfaction and wear compliance.

Therefore, there is a need for a solution that can better address the fitting process, the fit of a wearable to a wearer's body, and the maintenance of the fit throughout the wear time. Moreover, there is increasingly also a need for a solution that can alleviate the degree of physical contact between persons, as well as between persons and equipment/wearables, and thereby reduce any potential exposure to, and transfer of, communicable contaminants.

DESCRIPTION

The description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Wearables

A wearable medical device or system, also referred to here as wearable or wearables, can be a wearable defibrillator (WD) system, such as a wearable cardioverter defibrillator (WCD) system. A WCD system may protect a patient by electrically restarting their heart, if needed. Such a WCD system may have a number of components, also referred to here as elements. These components can be provided separately as modules and can be interconnected, or can be combined with other components, and so on. In some scenarios, a patient may be prescribed a WCD, and after some time, the patient may no longer need the therapy element or module, but would still be monitored for an additional period. In such cases, the WCD may be converted to a monitoring wearable.

Figure 1:
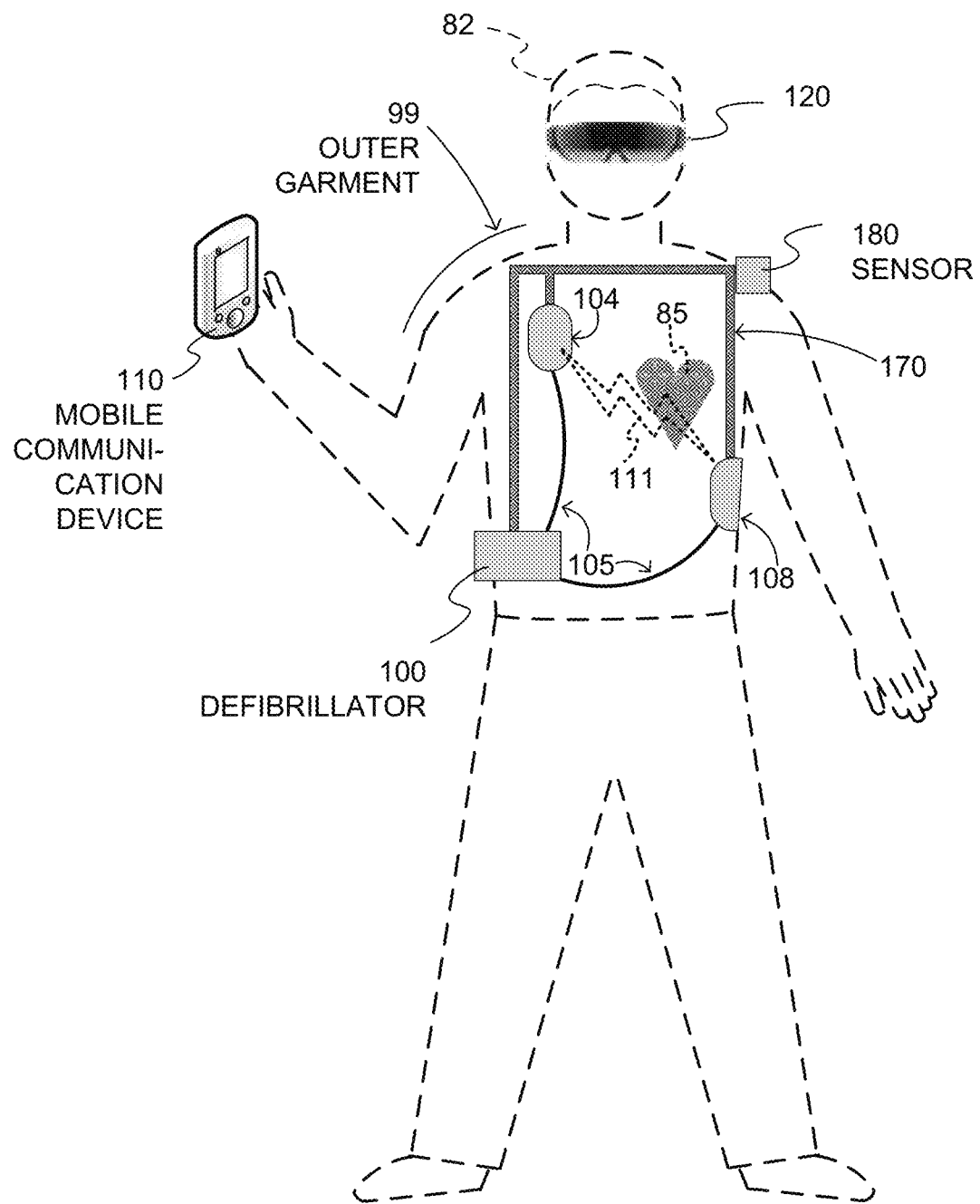
FIG. 1 is a conceptual diagram generally showing a wearable, similar to a wearable shown in FIG. 2, and examples of a fit assist device, in accordance with embodiments.

FIG. 1 depicts a patient 82. Patient 82 may also be referred to as a person, an individual, and/or wearer. The patient is wearing components of a wearable medical system, and more specifically a WCD system. The system includes one or more parts or elements, such as a garment, which can act as a scaffold for attachment of a wearable ECG and therapy electrodes, and/or the same or separate garment, such as a belt, which acts as a scaffold for a monitor. Any additional sensors or devices can be also removably attachable to either the garment or the belt, or other piece of clothing, and/or alternatively directly to a body part by an adhesive or other means. In a further example, a wearable can be one to be worn hidden under an attire or outer garment 99.

In embodiments of the present disclosure, the wearable includes a customizable scaffold or platform 170, such as a garment for attaching, detaching, reconfiguring, of different wearable elements, including electrodes 104, 108, defibrillator 100, other sensors 18, based on user or patient needs at different phases of a condition or health status.

A fit assist device can be implemented with a mobile communication device 110 (examples of which can be a mobile phone or a tablet), or a headwear device 120 (examples of which can be glasses or headset). The fit assist device can alternatively be in a form of a mirror, a scanning platform, or another device configured with similar functionalities to those described herein, etc.

The fit assist device comprises a fitting assistant application (app) configured to utilize at least one of augmented, virtual, and mixed reality capabilities. The fit assist device further comprises a communication module, which may be configured to interact with a remote professional fitting assistant, clinician, advisor, consultant, or a remote service. The fit assist device can comprise one or more processors, memory module, mirror, camera and/or video capabilities. Alternatively, the fit assist device can utilize certain capabilities already on the mobile device, for example camera, video, and the fitting assistant app can be implemented on, uploaded, and/or also interact with other applications, databases, devices, computer systems, smart wearables, fitting rooms, smart appliances, for example intelligent glasses or mirrors, displays, etc. For example, a patient avatar or a patient realistic 3D image, which can be dynamic or static, can feature wearables and be displayed on the mobile device or through headset, or alternatively on another computer or a large standing mirror display or monitor, etc. Specific, non-exhaustive examples of such embodiments are provided for completeness. These and other embodiments will be apparent to those skilled in the art upon a review of the description.

The fitting assistant app can be used to fit the WCD system with its various components to the wearer's body. The fit assist device and the app are described in further detail with reference to FIGS. 5-7 below.

Figure 2:
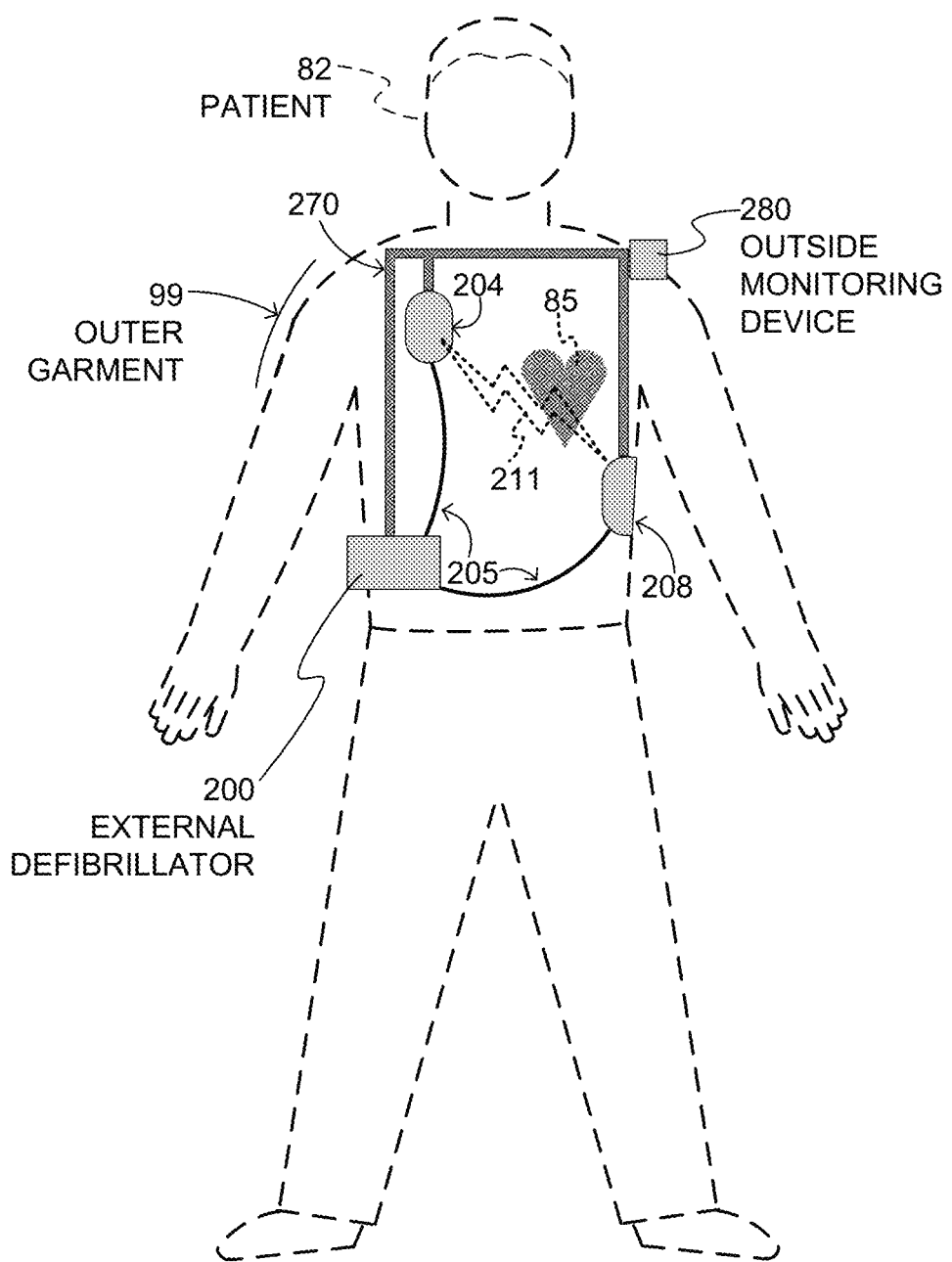
FIG. 2 is a conceptual diagram of a patient wearing a wearable medical monitoring system, such as a WCD, in accordance with embodiments.

FIG. 2 illustrates a wearer 82, who can be ambulatory patient, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT), a service representative, a fitting expert, a technician, or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In some instances, a WCD can be configured with AI guided customization, including fitting capabilities, as shown in patent application U.S. Utility patent application Ser. No. 16/946,512, filed on Jun. 24, 2020, titled: "Wearable Cardioverter Defibrillator With AI-Based Features," incorporated herein by reference in its entirety.

FIG. 2 also depicts components of a WCD system made according to embodiments. One such component is a support structure 270 that is wearable by ambulatory patient 82. Accordingly, support structure 2970 is configured to be worn by ambulatory patient 82 for at least several hours per day, and for at least several days, even a few months, or longer. It will be understood that support structure 270 is shown only generically in FIG. 2, and in fact partly conceptually. FIG. 2 is provided merely to illustrate concepts about support structure 270, and is not to be construed as limiting.

Support structure 270 can be implemented in many different ways. For example, it can be implemented in a single component or a combination of multiple components. In embodiments, support structure 270 could include a vest, a half-vest, a garment, a scaffold, etc. In such embodiments such items can be worn similarly to analogous articles of clothing. In embodiments, support structure 270 could include a harness, one or more belts or straps, etc. In such embodiments, such items can be worn by the patient around the torso, hips, over the shoulder, etc. In embodiments, support structure 270 can include a container or housing, which can even be waterproof. In such embodiments, the support structure can be worn by being attached to the patient's body by adhesive material, for example as shown and described in U.S. Pat. No. 8,024,037. Support structure 270 can even be implemented as described for the support structure of US Pat. App. No. US 2020/0222707, which is incorporated herein by reference. Of course, in such embodiments, the person skilled in the art will recognize that additional components of the WCD system can be in the housing of a support structure instead of being attached externally to the support structure, for example as described in the US2020/0222707 document. There can be other examples.

Support structure 270 and its components can be implemented by being fitted to a wearer's body using virtual and/or augmented and/or mixed reality (VR/AR/MR). Components such as a vest, a half-vest, a garment, a scaffold-like structure. Elements of the garment can be optimized for fit using of at least one of VR/AR/MR application on a fit assist device, which can be a mobile device such as a mobile phone, or another wearable, examples of which are shown in FIG. 1. Other wearable elements of the WCD can then also be fitted using AR/VR/MR.

FIG. 2 shows a sample external defibrillator 200. As described in more detail later in this document, some aspects of external defibrillator 200 include a housing and an energy storage module within the housing. As such, in the context of a WCD system, defibrillator 200 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 2 also shows sample defibrillation electrodes 204, 208, which are coupled to external defibrillator 200 via electrode leads 205. Defibrillation electrodes 204, 208 can be configured to be worn by patient 82 in a number of ways. For instance, defibrillator 200 and defibrillation electrodes 204, 208 can be coupled to support structure 270, directly or indirectly. In other words, support structure 270 can be configured to be worn by ambulatory patient 82 so as to maintain at least one of electrodes 204, 208 on the body of ambulatory patient 82, while patient 82 is moving around, etc. The electrode can be thus maintained on the body in a secured position by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 200 can be considered coupled to support structure 270 directly, or indirectly via at least one of defibrillation electrodes 204, 208. Optimization of positioning of the elements over organs of interest and coupling of the elements to the support structure 270 can be performed using VR and/or AR application. Proper securement of the elements and contact with a patient's body can help acquire good quality of ECG signal.

When defibrillation electrodes 204, 208 make good electrical contact with the body of patient 82, defibrillator 100 can administer, via electrodes 204, 208, a brief, strong electric pulse 211 through the body. Pulse 211 is also known as shock, defibrillation shock, therapy, electrotherapy, therapy shock, etc. Pulse 211 is intended to go through and restart heart 85, in an effort to save the life of patient 82. Pulse 211 can further include one or more pacing pulses of lesser magnitude to simply pace heart 85 if needed, and so on.

A defibrillator can decide whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 280. Device 280 is called an "outside" device because it could be provided as a standalone device, for example not within the housing of defibrillator 200. Device 280 can be configured to sense or monitor at least one local parameter. A local parameter can be a parameter of patient 82, or a parameter of the WCD system, or a parameter of the environment, as will be described later in this document.

For some of these parameters, device 280 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as physiological inputs and patient inputs. In embodiments, a sensor can be construed more broadly, as encompassing many individual sensors.

Optionally, device 280 is physically coupled to support structure 270. In addition, device 280 may be communicatively coupled with other components that are coupled to support structure 270. Such communication can be implemented by a communication module, as will be deemed applicable by a person skilled in the art in view of this description.

In embodiments, one or more of the components of the shown WCD system may be customized for patient 82. This customization may include a number of aspects. As mentioned above, support structure 270 can be fitted to the body of patient 82 using an augmented reality and/or virtual reality tools. Baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 3:
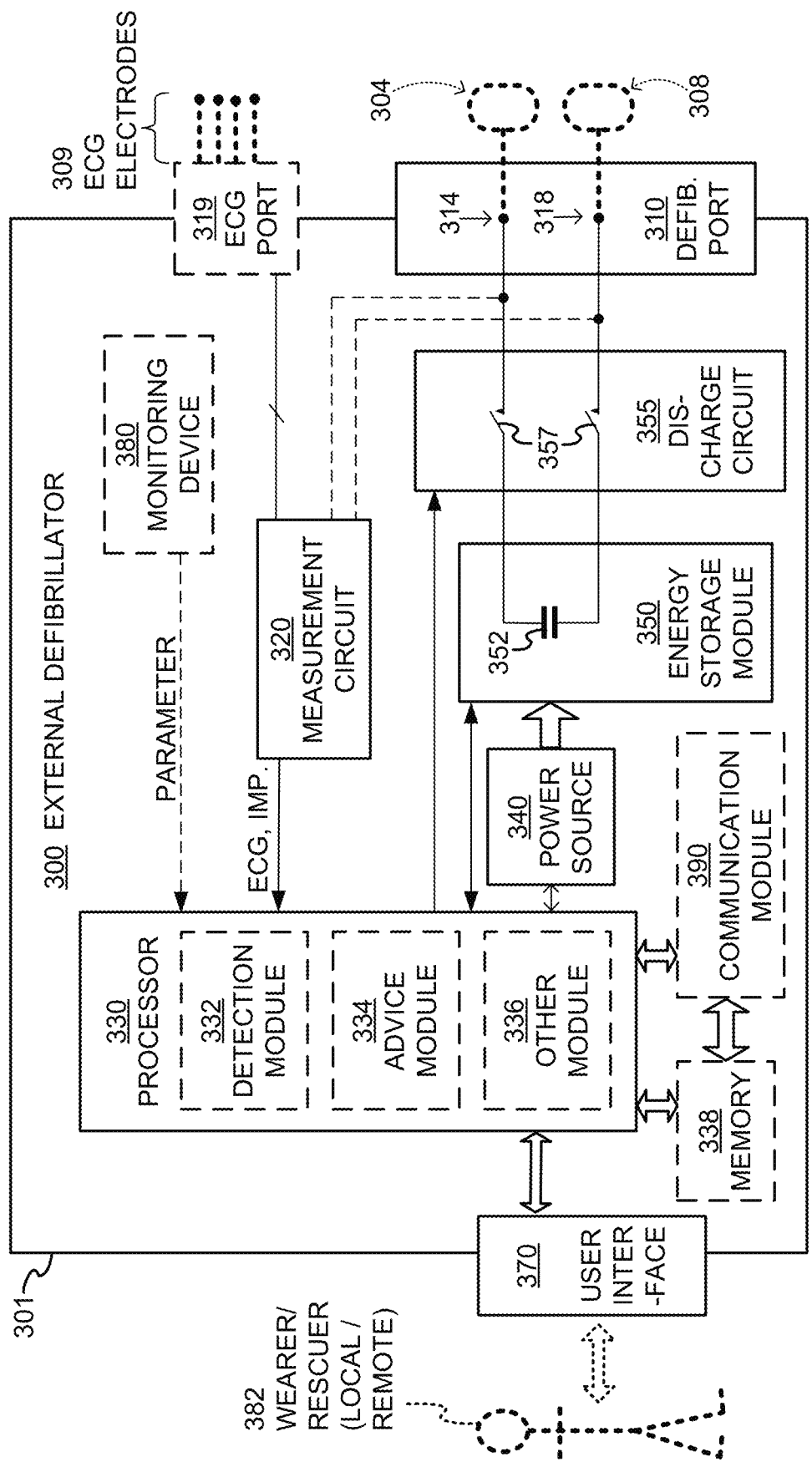
FIG. 3 is a diagram showing components of an external defibrillator, in accordance with embodiments.

FIG. 3 is a diagram showing components of an external defibrillator 300 made according to embodiments. These components can be, for example, in external defibrillator 100 of FIG. 1. The components shown in FIG. 3 can be provided in a housing 301, which is also known as casing 301.

External defibrillator 300 is intended to be worn by a patient, such as ambulatory patient 380. Defibrillator 300 may further include a user interface 370 for a user 382. User 382 can be patient 82, also known as wearer 82. Or, user 382 can be a local rescuer at the scene, such as a bystander who might offer assistance, a service representative, a fitting expert, or a trained person. Or, user 382 might be a wearer's personal caregiver, or a remotely located support in communication with the WCD system, and/or the wearer and/or the personal caregiver of the patient.

User interface 370 can be made in a number of ways. User interface 370 may include output devices, which can be visual, audible or tactile, for communicating to a user by outputting images, sounds or vibrations. Images, sounds, vibrations, and anything that can be perceived by user 382 can also be called human-perceptible indications (HPIs). There are many examples of output devices. For example, an output device can be a light, or a screen to display what is sensed, detected and/or measured, and provide visual feedback to rescuer 382 for their resuscitation attempts, and so on. Another output device can be a speaker, which can be configured to issue voice prompts, beeps, loud alarm sounds and/or words to warn bystanders, etc.

User interface 370 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 300 may include a housing 301 and a monitoring device 380. Monitoring device 380 can be integrated within the housing of the defibrillator 300 and monitor patient parameters, system parameters and/or environmental parameters. The monitoring device 380 can be complementary or an alternative to an external or a monitoring device outside the defibrillator 300, such as monitoring device 180 shown in FIG. 1. Allocating which parameters are obtained by which monitoring devices 180 or 380 can be done according to design considerations. Monitoring Device 380 may include one or more sensors.

Monitoring device 380 is configured to monitor at least one local parameter. A local parameter is a parameter of patient 382, or a parameter of the wearable defibrillation system, or a parameter of the environment. Optionally, monitoring device 380 is physically coupled to the support structure. In addition, monitoring device 380 is communicatively coupled with other components coupled to the support structure, such as a communication module, as will be deemed necessary by a person skilled in the art in view of this disclosure.

In some embodiments, the local parameter is a trend that can be detected in a monitored physiological parameter of patient 382. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 382 will know about a condition that is either not improving or deteriorating.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds, size changes, weight changes, pulse.

Accordingly, an additional or separate from the defibrillator, monitoring device 180, as shown in FIG. 1, may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, sensor detecting changes in body size, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

Patient state parameters include recorded aspects of patient 382, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place, or whether a patient's congestive heart failure (CHF) is worsening. A monitoring device 180 may include one or more sensors detecting additional patient state parameters, such as body dimensions and changes of dimensions. As a wearable system and/or its elements can be localized or distributed about a patient's body, such positioning around a patient's body can be further optimized using augmented, virtual, and/or mixed reality tools, which may include sensors configured to detect dimensions and/or changes in dimensions. Sensors can assist with physical dimension measurements of two-dimensional and/or three-dimensional physical features.

A WCD system made according to embodiments may thus include a motion detector. In embodiments, a motion detector can be implemented within monitoring device 180 or monitoring device 380. Such a motion detector can be made in many ways as is known in the art, for example by using an accelerometer. In this example, a motion detector is implemented within monitoring device 380. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 380 includes a GPS location sensor as per the above, and if it is presumed that the patient is wearing the WCD system.

Monitoring device 380 can comprise monitoring device 180, 280 or an accessory device such as a mobile communication device 210, or a headwear device 220, which can further include additional sensors and capabilities. For example, a sensor to detect and assist with measurements of physical dimensions, such as body dimensions, wearable device or sensor dimensions, or changes in dimensions of body of objects can be detected and utilized by the fitting process for fitting and/or further adjustments.

Defibrillator 300 typically includes a defibrillation port 310, which can be a socket in housing. Defibrillation port 310 includes electrical nodes 314, 318. Leads of defibrillation electrodes 304, 308, such as leads 105 of FIG. 1, can be plugged into defibrillation port 310, so as to make electrical contact with nodes 314, 318, respectively. It is also possible that defibrillation electrodes 304, 308 are connected continuously to defibrillation port 310, instead. Either way, defibrillation port 310 can be used for guiding, via electrodes, to the wearer at least some of the electrical charge that has been stored in an energy storage module 350 that is described more fully later in this document. The electric charge will be the shock for defibrillation, pacing, and so on.

Defibrillator 300 may optionally also have a sensor port in housing 301, which is also sometimes known as an ECG port 319. Sensor port 319 can be adapted for plugging in sensing electrodes 309, which are also known as ECG electrodes and ECG leads. It is also possible that sensing electrodes 309 can be connected continuously to sensor port 319, instead. Sensing electrodes 309 are types of transducers that can help sense an ECG signal, e.g. a 12-lead signal, or a signal from a different number of leads, especially if they make good electrical contact with the body of the patient and in particular with the skin of the patient. As with defibrillation electrodes 304, 308, the support structure can be configured to be worn by patient 282 so as to maintain sensing electrodes 309 on a body of patient 382. For example, sensing electrodes 309 can be attached to the inside of support structure 170 for making good electrical contact with the patient, similarly with defibrillation electrodes 304, 308. Positioning and attachments can be optimized using virtual and/or augmented reality comprising apparatus and method.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 304, 308, and for sensing electrodes 309.

The fluid may be initially stored in a fluid reservoir, not shown. Such a fluid reservoir can be coupled to the support structure. In addition, a WCD system according to embodiments further includes a fluid deploying mechanism. Fluid deploying mechanism can be configured to cause at least some of the fluid to be released from the reservoir and be deployed near one or both of the patient locations to which electrodes 304, 308 are configured to be attached to the patient. In some embodiments, fluid deploying mechanism is activated prior to the electrical discharge responsive to receiving activation signal AS from a processor 330, which is described more fully later in this document.

In some embodiments, defibrillator 300 also includes a measurement circuit 320, as one or more of its working together with its sensors or transducers. Measurement circuit 320 senses one or more electrical physiological signals of the patient from sensor port 319, if provided. Even if defibrillator 300 lacks sensor port, measurement circuit 320 may optionally obtain physiological signals through nodes 314, 318 instead, when defibrillation electrodes 304, 308 are attached to the patient. In these cases, the input reflects an ECG measurement. The patient parameter can be an ECG, which can be sensed as a voltage difference between electrodes 304, 308. In addition, the patient parameter can be an impedance, which can be sensed between electrodes 304, 308 and/or between the connections of sensor port 319 considered pairwise. Sensing the impedance can be useful for detecting, among other things, whether these electrodes 304, 308 and/or sensing electrodes 309 are not making good electrical contact with the patient's body. These patient physiological signals may be sensed when available. Measurement circuit 320 can then render or generate information about them as inputs, data, other signals, etc. As such, measurement circuit 320 can be configured to render a patient input responsive to a patient parameter sensed by a sensor. In some embodiments, measurement circuit 320 can be configured to render a patient input, such as values of an ECG signal, responsive to the ECG signal sensed by sensing electrodes 309. More strictly speaking, the information rendered by measurement circuit 320 is output from it, but this information can be called an input because it is received as an input by a subsequent device or functionality.

Defibrillator 300 also includes a processor 330. Processor 330 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of executable instructions so as to offer or fulfill a particular functionality. Embodiments of modules and the functionality delivered are not limited by the embodiments described in this document.

Processor 330 can be considered to have a number of modules. One such module can be a detection module 332. Detection module 332 can include a Ventricular Fibrillation (VF) detector. The patient's sensed ECG from measurement circuit 320, which can be available as inputs, data that reflect values, or values of other signals, may be used by the VF detector to determine whether the patient is experiencing VF. Detecting VF is useful, because VF typically results in SCA. Detection module 332 can also include a Ventricular Tachycardia (VT) detector, and so on.

Another such module in processor 330 can be an advice module 334, which generates advice for what to do. The advice can be based on outputs of detection module 332. There can be many types of advice according to embodiments. In some embodiments, the advice is a shock/no shock determination that processor 330 can make, for example via advice module 334. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul.

17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference for all purposes.

Processor 330 can include additional modules, such as other module 336, for other functions. In various embodiments, other module 236 may include functional instructions for performing machine learning or artificial intelligence functions. Examples of such functional instructions may be implemented as a neural network, random forest, a support vector machine, recursive partitioning, Bayesian methods, fuzzy rule-based systems, or the like. One or more of such other modules 336 may be configured to implement various embodiments of artificial intelligence functions described below. "Artificial Intelligence" or "AI" technology can be applied to Wearable Cardioverter Defibrillators ("WCDs") and other wearable medical equipment in various ways, including garment fitting and adjustment, as further disclosed in U.S. patent application Ser. No. 16/946,512, filed on Jun. 24, 2020, titled: Wearable Cardioverter Defibrillator With AI-Based Features, incorporated herein by reference in its entirety.

Defibrillator 300 optionally further includes a memory 338, which can work together with processor 330. Memory 338 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 338 is thus a non-transitory storage medium. Memory 338, if provided, can include programs for processor 330, which processor 330 may be able to read and execute. More particularly, the programs can include sets of instructions in the form of code, which processor 330 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 330, and can also include protocols and ways that decisions can be made by advice module 334. In addition, memory 338 can store prompts for user 382, if this user is a local rescuer. Moreover, memory 338 can store data. This data can include patient data, system data and environmental data, for example as learned by internal monitoring device 380 and outside monitoring device 180. The data can be stored in memory 338 before it is transmitted out of defibrillator 300, or be stored there after it is received by defibrillator 300.

Defibrillator 300 can optionally include a communication module 390, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 390 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 390 may also include such interconnected sub-components as may be deemed necessary by a person skilled in the art, for example an antenna, portions of a processor, supporting electronics, outlet for a telephone or a network cable, etc.

Defibrillator 300 may also include a power source 340. To enable portability of defibrillator 300, power source 340 typically includes a battery. Such a battery is typically implemented as a battery pack, which can be rechargeable or not. Sometimes a combination is used of rechargeable and non-rechargeable battery packs. Other embodiments of power source 340 can include an AC power override, for where AC power will be available, an energy-storing capacitor, and so on. Appropriate components may be included to provide for charging or replacing power source 340. In some embodiments, power source 340 is controlled and/or monitored by processor 330.

Defibrillator 300 may additionally include an energy storage module 350. Energy storage module 350 can be coupled to the support structure of the WCD system, for example either directly or via the electrodes and their leads. Module 350 is where some electrical energy can be stored temporarily in the form of an electrical charge, when preparing it for discharge to administer a shock. In embodiments, module 350 can be charged from power source 340 to the desired amount of energy, as controlled by processor 330. In typical implementations, module 350 includes a capacitor 352, which can be a single capacitor or a system of capacitors, and so on. In some embodiments, energy storage module 350 includes a device that exhibits high power density, such as an ultracapacitor. As described above, capacitor 352 can store the energy in the form of an electrical charge, for delivering to the patient.

A decision to shock can be made responsive to the shock criterion being met, as per the above-mentioned determination. When the decision is to shock, processor 330 can be configured to cause at least some or all of the electrical charge stored in module 350 to be discharged through the body of patient 82 while the support structure is being worn by patient 82, so as to deliver a therapy shock 111 to patient 82.

For causing the discharge, defibrillator 300 moreover includes a discharge circuit 355. When the decision is to shock, processor 330 can be configured to control discharge circuit 355 to discharge through the patient at least some of all of the electrical charge stored in energy storage module 350. Discharging can be to nodes 314, 318, and from there to defibrillation electrodes 304, 308, so as to cause a shock to be delivered to the patient. Circuit 355 can include one or more switches 357. Switches 357 can be made in a number of ways, such as by an H-bridge, and so on. Circuit 2355 could also be thus controlled via processor 330, and/or user interface 370.

A time waveform of the discharge may be controlled by thus controlling discharge circuit 355. The amount of energy of the discharge can be controlled by how much energy storage module has been charged, and also by how long discharge circuit 355 is controlled to remain open.

Defibrillator 300 can optionally include other components.

Figure 4:
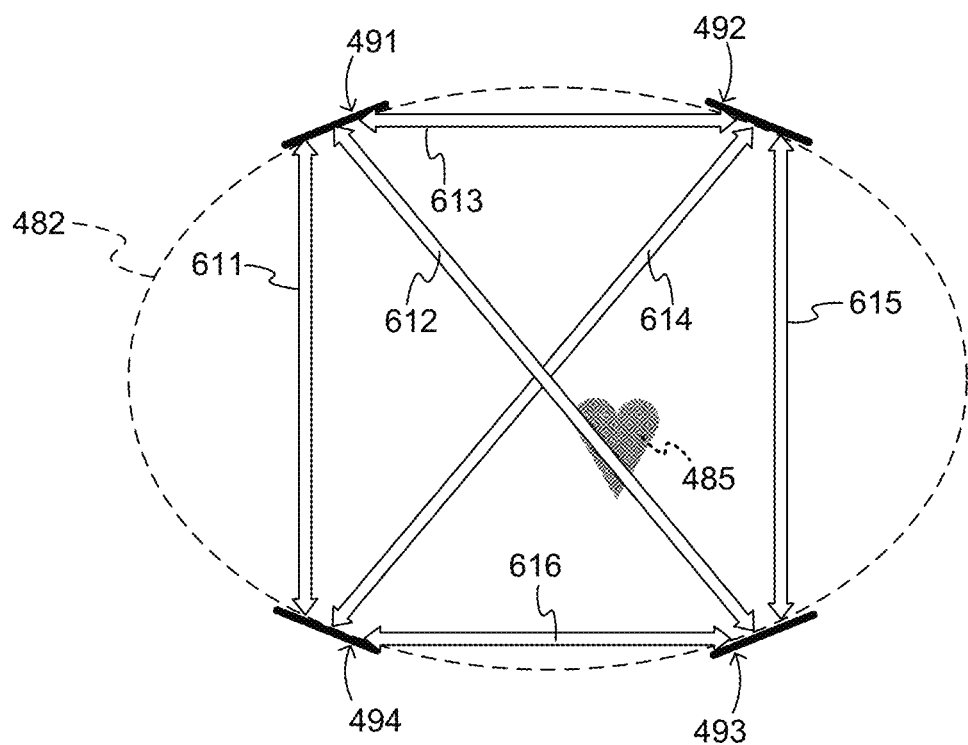
FIG. 4 is a conceptual diagram for illustrating how multiple electrodes of a WCD system may be used for sensing ECG signals along different vectors, in accordance with embodiments.

FIG. 4 is a conceptual diagram for illustrating how multiple electrodes of a WCD system, which may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 need to be maintained on the torso of patient 482, and any of their respective wire leads and cables (not shown) need to be comfortably secured as well. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 411-416, which also create ECG channels.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "Wearable Cardioverter Defibrillator Components Making Aggregate Shock/No Shock Determination from Two or More ECG Signals", which is incorporated herein by reference.

In embodiments, to make the shock/no-shock determination as correctly as possible, an accurate placement of the ECG electrodes is important in obtaining good quality signals, rhythm analysis, and interpretation.

It should be remembered that the person wearing the wearable defibrillator system may be moving, for example during their daily activities and the system or individual elements may need to be repositioned. The patient may take a shower and remove the system to take a shower, for example, and will need to position the support structure and couple the detachable elements afterwards.

Wearable Fit Assist

Generally stated, various embodiments may implement artificial intelligence, machine learning, augmented, virtual, and/or mixed reality tools to assist various functions and/or fitting of a wearable device system, such as a WCD system, to a wearer's body.

Virtual Reality (VR) as disclosed herein should be understood as technology that can immerse one in a virtually-created, computer-generated environment.

Augmented reality (AR), as disclosed herein, should be understood as technology that can superimpose or overlay virtual images over the real-world environment or objects. Alternatively, AR can import real world images into the virtual world. VR or AR can be applied to customize a fitting of a wearable health or medical system, such as a wearable monitoring and/or treatment system as described further herein.

Mixed reality (MR) should be understood as technology that can be advanced AR where a user can interact with virtual objects, can manipulate the objects, can view them from different angles, etc., while remaining in a real-world environment, or alternatively, it can be an advanced form of VR, but one where the virtual overlaps the real world with the objects in it, or becomes a virtual replica of the real world and stays anchored with it.

In one scenario, a patient is prescribed a wearable monitoring and treatment system such as depicted in FIGS. 1-5. FIGS. 5A and 5B are diagrams of sample embodiments of components of a WCD system as fitted to a body of a wearer. The fitting can be performed using a fitting assistant app implemented on a fit assist device, such as a mobile device, shown in FIG. 5B, and similar to a mobile device 110, illustrated in FIG. 1.

Figure 5A:
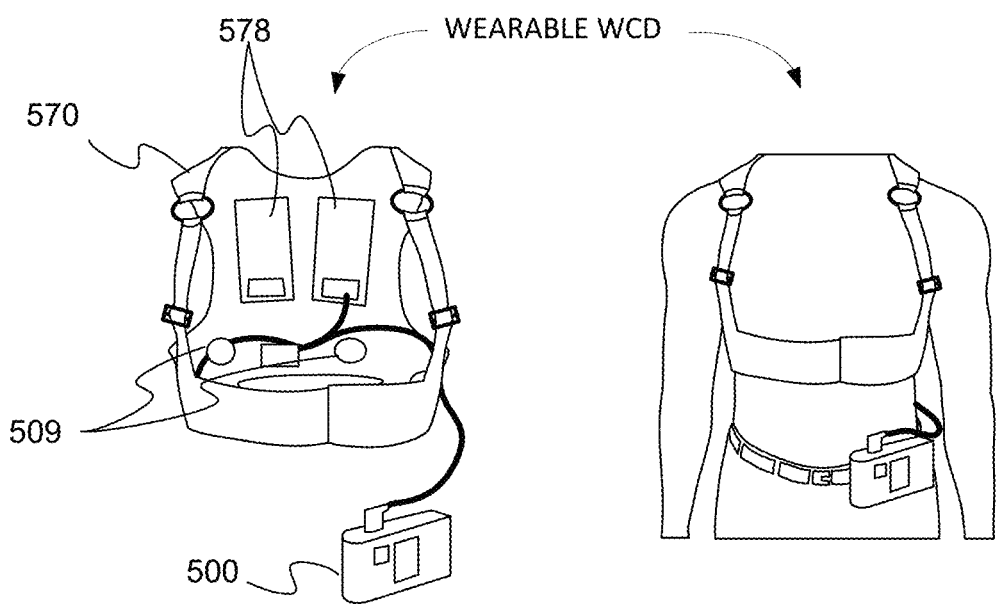
FIG. 5A is a diagram of sample embodiments of components of an WCD system as applied to a wearer, in accordance with embodiments.
Figure 5B:
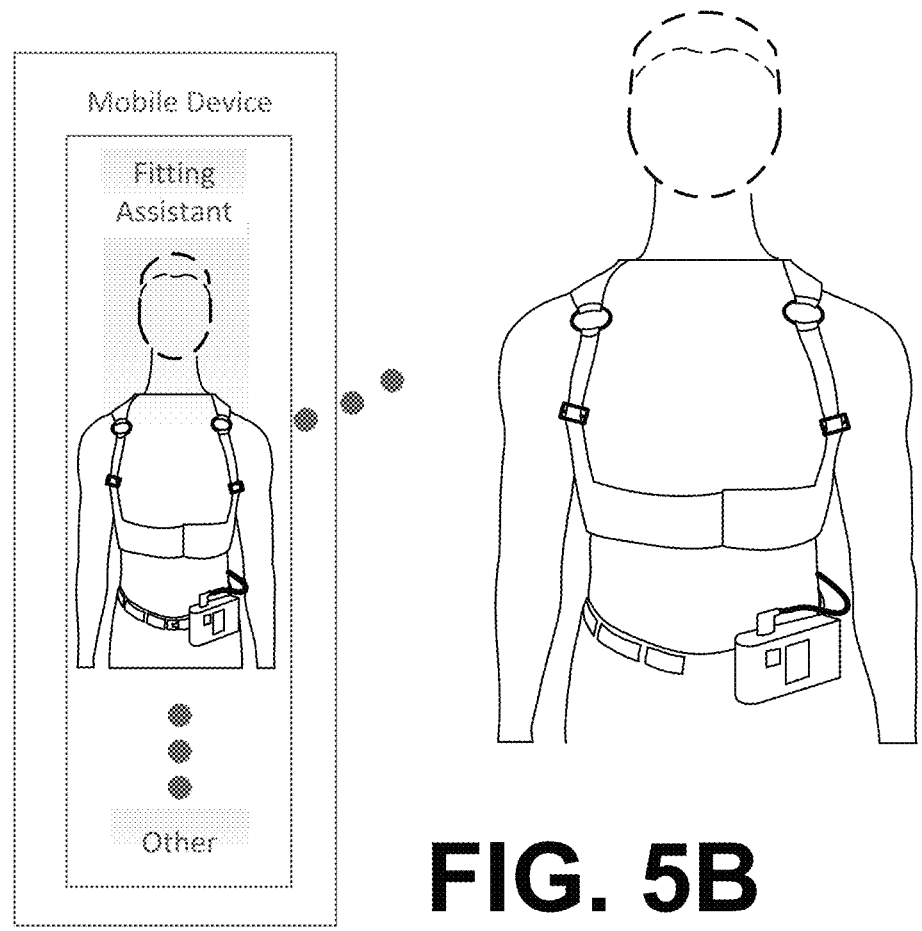
FIG. 5B is a diagram of a sample embodiment of a fit assist device featuring a fitting assistant application (app), in accordance with embodiments.

As can be understood from FIGS. 5A and 5B, a support structure 570 includes a vest-like wearable garment. The WCD system also includes an external monitor, which includes a defibrillator 500. The external monitor 500 may be carried in a purse, pouch, backpack, on a belt, by a strap over the shoulder, and so on. Alternatively, the monitor can be worn by attachment means to a wearable scaffold, such as the wearable garment. Wires connect the defibrillator 500 to sensing and defibrillation (also referred to as therapy electrodes) electrodes 578.

In embodiments disclosed herein, support structure 570 is fitted to be worn by an ambulatory patient so as to maintain sensors, such as sensing ECG electrodes 509 on a body of the patient in specific regions with the intent to optimize the quality of sensed physiological signals, such as ECG signals from the heart, as well as to optimize patient wear comfort, look, etc. The WCD's back therapy defibrillation electrodes 578 need to be securely maintained in place and in contact with the back of the patient. For example, defibrillation electrodes can be secured in pockets of the garment. Therapy delivery decisions are based on information provided by sensing ECG electrodes 509. Thus, the sensing electrodes need to be maintained securely in positions and in a best possible contact with patient's body as well.

If not positioned and maintained correctly, ECG signals from the sensing electrodes may include too much noise to be useful. To ameliorate the problem, multiple ECG sensing electrodes can be provided, for presenting many options to processor. These options are different vectors for sensing the ECG signal, as illustrated in FIG. 4. Ensuring that a wearer's comfort and a proper contact between electrodes and the wearer's appropriate body parts are maintained throughout the wear time, can further ameliorate this problem. To help achieve both the contact and the comfort, fitting can be informed with AR/VR/MR features.

In embodiments, a fit assist device can be configured with at least one of a virtual, augmented, and/or mixed reality (VR/AR/MR) database comprising content related to the wearer and the wearable. The fit assist device's sample components can include a three-dimensional (3D) sensor, a scanner, a camera, a video camera, a mirror, a processor, a display, a communications module, a fitting assistant app with a fitting match and overlay feature, which uses two-dimensional (2D), 3D data points, and can superimpose augmented reality objects onto physical objects. The fit assist device further comprises various data files, databases cataloging both wearer and wearable and comprising real, AR, VR, reference such as anatomical database. Other components are possible.

In some embodiments, a library of reference guides, and/or video or a library of videos guiding through how to put the WCD on, how to take it off, what to do if this or that happens, how to take it apart for washing the garment, whom to contact with questions, provide feedback, etc., can be uploaded to the wearer's mobile device and/or fit assist device. Other components are possible. Other databases can be interfaced with, updated, added or removed.

The sample components of the fit assist device can be utilized in creating one or more configurations of a fit and optimizing the outcome, one that a patient and a clinician/prescriber can approve, for example. The fit configurations can help a wearer and/or a user see visual representations of the wearable elements' distribution around the wearer's body, front, back, sides, etc. If adjustments are made, the configurations can be saved for comparison. The patient may be encouraged to perform usual daily activities to anticipate any adjustments. The profile and history of wear and use, and any patient feedback can inform next steps, interventions, adjustments, etc. In some embodiments, an AR customized wearable system can be created for a similar population or group of patients.

The AR/VR/MR database(s) can also include database comprising outer garment options. Sample components of the fit assist device also include wearable components and/or the wearer's various physical parameters.

The fit assist device can be configured to detect and obtain 2D and/or 3D data points about a physical object and/or wearer's physical features. Real time images of the patient's body physical features can be obtained and counterpart augmented and virtual reality for these features created in an avatar. Augmented, virtual, and/or mixed reality of data files of at least one or more of the elements of the wearable system, sizes, body placement areas, etc., can be stored, cataloged, and retrieved.

A wearer's physical parameters' database can include digitized realistic representations, as well as augmented and/or virtual counterparts, and can further include any internal imaging databases, including generic anatomy and physiology based on a wearer's gender, scanned sensor and template database, fitting overlay match output database, as well as mirror, camera, video, 2D/3D image database. Similarly, wearable components', such as WCD components', database can include realistic, augmented, and/or virtual counterparts.

To obtain external dimensions, contours, width, height, depth, etc., the fit assist device can use one or more points of reference and scan the physical feature of the wearer that will support the scaffold 170 and also relevant medical wearables. ECG, therapy, and other wearable elements positions can be determined and fitted over the scaffold.

The scan of the physical features can be facilitated by camera and/or video images and/or three-dimensional sensor. Body regions for accurate placement of sensors, electrodes, therapy pads, monitor, etc., can be further assisted with internal imaging and/or internal organ visualizations vis-à-vis wearable placement.

A point or map of reference can be used to obtain more accurate physical dimensions. The point of reference can be facilitated by a scannable tag, a grid, a map, or another object such as mirror, etc. In one embodiment, a physical garment can be configured to provide a reference map. The reference point or map can be on the scaffold 170, which also supports the wearable parts/elements. In another embodiment, a "fitting-reference-finding purpose-only" garment can be used. The garment may comprise a tag, a gridline, or some other type of reference that helps obtain the dimensions using AR. These tags, gridlines, or other shapes of references can be scannable, such as a QR code. In yet another embodiment, the fit assist device can comprise a mirror with embedded point or map of reference.

The fit assist device can also include or access other physiological and anatomical database, which may be generally gender based, such as widely available anatomical apps featuring anatomy and physiology in 3D, or more individualized to a patient's population group, or even the patient. Anatomy can be as detailed or as filtered for specific organs of interest, for example heart and its actual location within the individual's thorax, as desirable. The fit assist may, in some embodiments, offer individualized patient data using wearer's internal organ imaging, radiography, MRI, ultrasound, angiography, to localize placement of electrodes and other sensors.

The fit assist device can be used by the wearer him/herself to obtain images and dimensions and to display one or more configurations of the wearable superimposed over the wearer's body using at least one of an augmented, virtual, and/or mixed reality configurations. The fit assist device can also be used by a user who may not necessarily be a wearer, for example a fitting human expert or a medical doctor, a nurse, a patient representative, a caregiver, etc., to obtain images and dimensions of the patient's physical characteristics. The wearer may not need to be physically present in the same room as the fitting expert, but they could communicate over telenetwork to guide the wearer with proper measurement taking and/or scanning using the fit assist. Backup tools like measuring tape can further be used to obtain physical parameters in certain situations. The wearer and/or fitting expert can also take images and display the wearable elements over the images, which can be helpful in further training the wearer and/or caregiver.

In embodiments, upon prescription of the wearable to a patient, a request for fitting can be sent to a fitting expert, or a clinician, for example, who can assist a patient in an initial fitting of the system, its elements, etc. In some scenarios, a mobile device can be assigned to the patient. The mobile device can comprise a fit assist device with a fitting assistant app, which can help to introduce and accustom the patient and/or patient's personal caregiver to the wearable, to train the patient or a caregiver on proper placement, adjustments, removal, wash, etc.

In one embodiment, a patient and/or caregiver can also be enabled to utilize a fitting assistant app, which can be configured help the patient with the initial fitting in comfort and privacy without the need for additional physical presence of other people. The fitting assistant app can be configured with an augmented, virtual, and/or mixed reality capability, and can walk the patient through the steps to get the wearable fitted, display the look of the wearable over the patient's body, help the patient learn about the wearable, how to put it on, how to remove it, how to adjust it, how to supply feedback and request reconfigurations to aid fit, comfort and monitoring data acquisition. A human expert can be still made available to the patient to supplement information, assist with any questions or requests, as needed.

In further embodiments, the fitting assistant app can provide an ability to feature different acceptable and not acceptable configurations, interactions with digital counterparts of the wearable and/or the wearer, proper and improper placement, etc. Virtual and/or augmented reality counterparts/representations of a product can be cataloged for future retrieval and re-fittings, and/or as an option library to consider. A user, who can be the wearer or another person in wearer's care network, can manipulate objects and score different configurations according to comfort level, for example.

The wearer with the superimposed digital representation of a wearable garment and/or device may engage in daily activities. Wearer's activities can be analyzed and used as a feedback for fitting. Such activities can involve activities that, for example, affect the positioning, adherence, tightness, friction, pressure points, loss of contact, etc.

In further example, a wearable can be one to be worn hidden under an attire or outer garment 99, as indicated in FIG. 1. A wearer can wear different types of outfits, for example what a wearer typically wears during a week and the AR/VR/MR feature can learn and display the interaction between the wearable and the overlaying clothes, including how different types of clothes may affect positioning of the wearable sensors. A series of images or a video can be taken, and recommendations are provided for placement. Based on a learning module's observations and any other data input, the fitting assistant app can provide recommendations as to how, for example ECG electrodes or other sensors behave underneath a particular exterior garment, such as tight-fitting athletic garment, work attire, or casual attire, and during various activities. The fitting assistant app can then provide recommendations for placement and/or different settings depending on the type of attire or activity. The fitting assistant app can also be used to fit outer garment over the wearable and display the look to the wearer. Additionally, the fit assist device can provide access to purchase outer garment options based on the fit performed.

WCD with AI functionality, as a system, can aid with a long-term monitoring, learning, care and support. For example, a WCD system with AI functionality can convey certain information that then a fit assist device can use. Such a system can anticipate changes as it acquires and learns about the wearer and the wearable, and provide notices of a change or notice to anticipate changes along with a time window in which the system needs attention and updates.

Different scenarios may be encountered, for example, a patient is overweight and fatty portions of the patient's body roll or undulate, causing the ECG sensors to move around or even lose skin contact, which in turn increases noise on the ECG signal or loss of signal. The WCD system can observe patient's body interaction with the electrodes and recommend locations on the body that where the sensors adhere better and longer due to less or no movement or where the body fat barrier is lessened or not present, and still obtain monitoring information. Further recommendations can be provided that anticipate next steps, actions, remedies, instructions to the wearer, alerts to the system, a "fitter" other than wearer, a clinician, or centralized remote care station. In another example, a person's body part may have extra folds of fatty tissue that impedes the placement or the site is not practicable. An alternate site may need to be used.

Other scenarios may involve wearer's more than normal perspiration. Wearer's body type, scaring, former injuries may also affect how and where a wearable should be placed.

In yet another scenario, a wearable monitoring system may be recommended for a very long period of time, for example months to years in cases where the wearable may be health monitoring on sustaining device, such as an insulin or dialysis systems. In other cases, a wearable can be an extension of one's body, such as an extremity, for example an amputee's arm, hand, leg, etc. There may be cases where a person may rely on the wearable as they are growing up, that is they change with time. In such cases, relevant data and feedback during the fitting process can be incorporated into decision-making as to device/sensor placement, overall wearable's size, comfort, etc. The fitting assistant can aid in long-term planning, alerting to sudden changes, scheduling of future modifications, replacements, subsequent fittings, updates to the system, device.

In another scenario, if a pregnant woman wears a monitoring system over extended period during her pregnancy, chances are the rate at which her body changes is fairly high. A wearable system, such as an ECG monitoring system, would need to change along with her changing body. In another example, a person loses weight and the wearable no longer fits or adheres properly. Here too, the wearable would need the wearable's size and positioning may need to be adjusted.

Feedback from the AR/VR fitting process can help assisting personnel, whether physically present or remote, to further modify any matching of the wearable to the wearer's body part. The feedback can be conveyed to the wearer's health care providers, product service representatives, professional fitters who work with the patient and anticipate present or future replacements, changes, or any other alterations. The feedback can also aid in estimating time for when such changes should be anticipated and to facilitate timely support for the system and the wearer.

In another embodiment, a wearer can be offered a mock-up wearable garment, device, or wearable system to wear throughout a predetermined fitting phase, for example through normal day's or week's activities, sleep, activities such as exercise, etc. A wearer can interact with the mock-up device or system, which can aid in collecting information on wearability, that is the wearer's comfort and interactions, etc. Any feedback for updates, changes or replacements is taken into consideration. The fitting assistant application can be applied as the wearer wearing the mock-up system and with feedback can help spot and baseline interactions, behaviors, and potential issues. If a wearable device is one that would be typically worn hidden under other garments, a variety of device-overlaying garments can be tried, or garments a wearer would normally wear, whether professional outfit, active clothes, pajamas, or comfort clothes can be used to superimpose the mock-up garment and assess the human, device, garment wearability, comfort, data acquisition impact. This approach can serve as a training period for both the wearer and the AR/VR/MR systems.

Whether the AR-only fitting, or AR/VR/MR-assisted fitting, or a fitting that requires a mock-up device, or all three should be implemented, can be determined based on a wearer's individual case. For example, in some cases no mock-up fitting phase is needed, while in other cases of extended wear time where the device must stay on 24/7, a mock-up use and training may be useful.

Information learned can be used to build or continue building the wearer's wear profile and design and re-design wearability as needed throughout any extended wear time and the wearer's changing physical condition or preferences. Positioning of sensors and device modules can be manipulated for optimal patient comfort and functionality. Optimal placements/positioning of sensors and devices can be achieved using physiologic information and physical augmented reality data points along with information as to human factors and historical data comprising comfort and other as provides by various sources, including updates from the patient on wearability, comfort, use, look, etc. During the wear time(s) the system can learn and be responsive to the wearer's needs and adjustments, as described in commonly-owned, U.S. patent application Ser. No. 16/946,512; Title: Wearable Cardioverter Defibrillator with AI-Based Features.

In another embodiment, AR/VR/MR assisted fitting can be done by a non-wearer physical person who is, for example, a fitting professional. The fitting can be performed during an in-person visit, or remotely. The professional fitting expert/consultant and the wearer and/or wearer's personal caregiver can interact during and post-fitting via video conferencing features, such as FaceTime, Microsoft Teams, Skype, Zoom, etc., or any other teleconferencing capabilities, including telemedicine capabilities in real time and/or can be recorded and sent to a designated person or location for preparation and assembly of the customized physical system. A fitting professional can be a service representative, and can also assist with any later changes or adjustments to the wearables. Alternatively, such fitting can be done by the patient him/herself or another person. The fitting may also be done at a doctor's or clinician's office, or any other setting.

In further embodiments, the fitting process can be optimized using a fitting assistant app with virtual, augmented, and/or mixed reality configurations. In one example, a 2D or 3D digital replica/counterpart of a product can be used to overlay a person's body. Alternatively, Digital representations can include virtual representations of both the wearer and the wearable. During an initial introduction of the patient to the concept of the wearable, both the patient and wearable representations can be virtual. As the fitting processes progresses, augmented aspects can be helpful to visualize the wearable on the wearer's body, and also perhaps train the wearer as well.

In further embodiments, additional information can be integrated into decision and fit process, including information from the WCD or external sensors 180, such as environmental information (e.g., motion, gait, activity, steps, posture, temperature, humidity, ECG fall off, or any of the other non-patient information described above) as well as patient information (e.g., heart rate, ECG, blood pressure, pulse oximetry, or any of the other patient-related information described above) can be used to further optimize the fit, wear and data quality.

An individual or a group within a population of patients can be spared the hassle of time-consuming and cumbersome physical appointments, travel, "try-on" fittings and "make-do" tailoring attempts at adjustments. Remote tools configured with virtual, augmented, and/or mixed reality (VR/AR/MR) assisted fitting of a wearable medical device and/or garments can facilitate and also improve customer experience from the initial interaction and throughout the extended wear time, as well as optimize fitting professional services resources.

In embodiments, a wearer, or a user of a wearable other than the wearer, for example a clinician, a caregiver, a fitting expert, a service representative, etc., can remotely assist in the process of fitting the wearable to the wearer's body. In one embodiment, a fit assist device comprising a fitting assistant app can be used to a wearer's physical parameters, images, dimensions, etc. The fit assist device can be a standalone device or can be included within another device, such as a cell phone, a headset, a laptop, a tablet, a mirror, a smart gadget, etc. The fit assist device can include a library of fitting videos, images which can be retrieved at a later time to refresh recollection on how to properly put the wearable on, take it off, adjust it. The fitting assistant app can utilize augmented, virtual, and/or mixed realty configurations to create displays in one or more configurations of the wearable superimposing the wearer's physical body region. The fitting assistant app can have realistic or a digital virtual replica avatar, representations of the wearer as well as the wearable to illustrate the placement and look. A wearer can provide adjustment requests and feedback for reevaluation and updates. Based on the information obtained by the fit assist device, remotely located experts can weigh in as needed to address additional issues or questions. The fitting assistant app can further assist the wearer to also select clothing, garments, that can go with the wearable, help with comfort, accessibility to the wearable while also, for example help maintain inconspicuous concealment of the wearable, etc.

Based on the provided feedback, updates in data, machine learning methods can be implemented and can create a wearability/fit models that can then aid updates and improve customization and adjustment to future fitting models.

Figure 6:
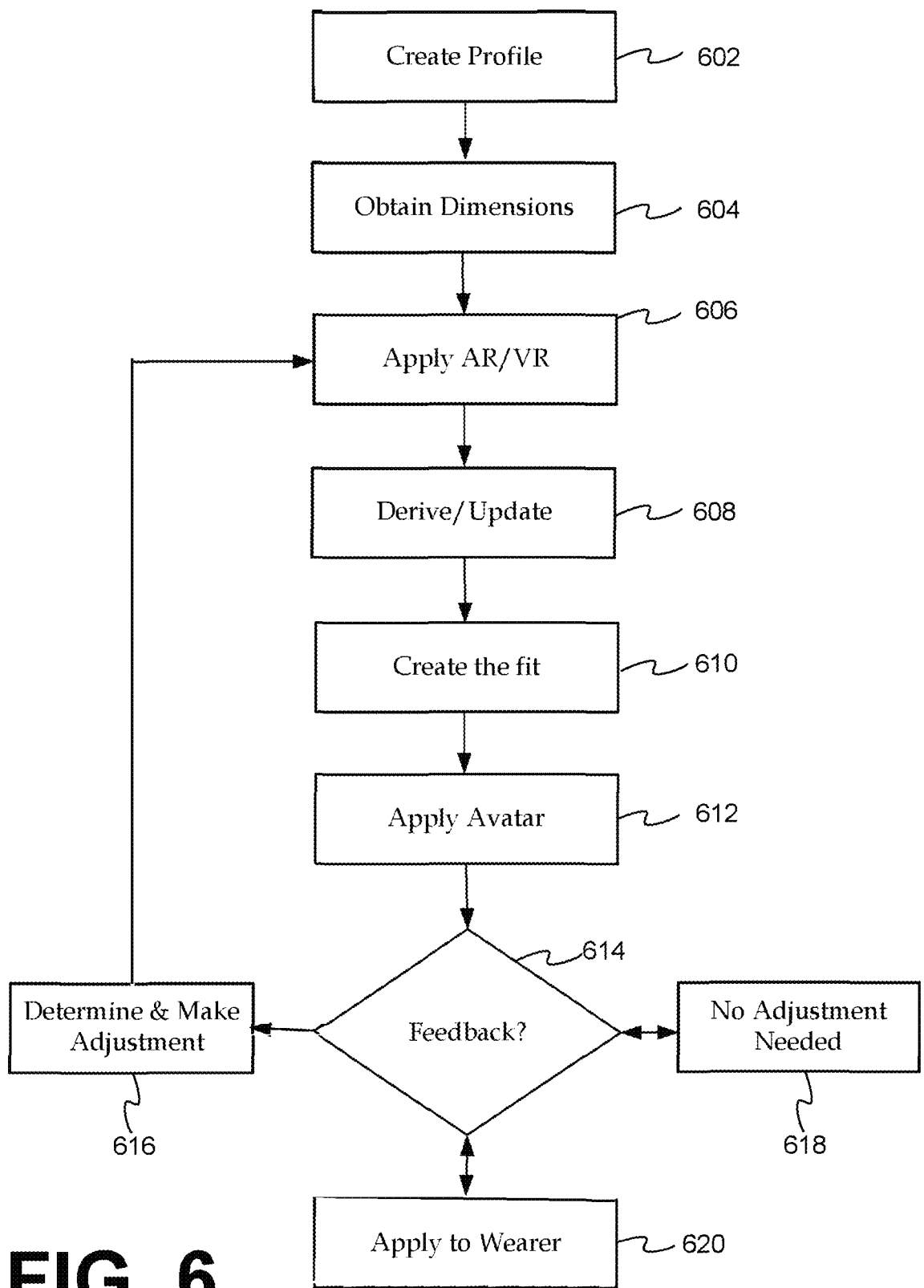
FIG. 6 is a flowchart of a method for fitting of a wearable to a patient using augmented and/or virtual reality (AR/VR), in accordance with embodiments.

FIG. 6 is a conceptual flow diagram generally illustrating an example AR/VR/MR fitting process. In this embodiment, initial profile is created 602 by inputting initial data. In one embodiment, in step 602 the fit assist device can be used to obtain relevant intake data of a wearer to create a digital profile and also an avatar reflective of the wearer. The initial data can include, but is not limited to, the wearers information such as name, login, personal preferences, medical information that may be relevant, etc. Once the profile is created, dimensions are obtained 604. Estimated sizes of the body part to support the wearable, and any other information such as torso size, shape, length, width, depth, height, weight, etc. Given the profile and dimension information, at least one of AR, VR, MR fitting tools and techniques are engaged and applied 606 to derive and update 608 and create a fit 610 by applying an avatar 612. A feedback 614 is used to either confirm that no adjustment is needed 618 or that an adjustment is needed 616, in which case, adjustment can be made via steps 606, 608, 610, 612 and as further described below. As mentioned throughout the description, feedback can come from a variety of sources, including the wearer, a caregiver, a fit expert, wear's databases, or the WCD system after being worn for some time as further described in the U.S. Utility patent application Ser. No. 16/946,512, filed on Jun. 24, 2020, titled: "Wearable Cardioverter Defibrillator With AI-Based Features," incorporated herein by reference in its entirety for all purposes.

Embodiments disclosed herein include methods to optimize fitting of a wearable cardioverter defibrillator system to a wearer's body in an augmented, virtual, and/or mixed reality configurations. One method includes creating a wearer's profile from an initial data, obtaining initial parameters and/or dimensions, such as height, weight, size, gender. The method further includes obtaining images and/or dimensions using a camera and/or a sensor configured to obtain dimensional parameters. A fit is created based on the initial data, images, and sensed dimensional parameters. Virtual counterpart of the wearer can be created and stored in a memory. The method includes storing augmented reality and virtual reality files which are counterparts to the wearer's physical characteristics and the wearables physical characteristics files. Data files can also include a selection of augmented and/or virtual reality choices for a wearer or a user to select from and assessment of a fit in relation to other selections. A user, who can be a wearer, a prescriber of a wearable, etc., can use a feedback as to comfort level and the fit as well as data quality.

In embodiments provided here, a three-dimensional sensor obtains information about physical features of a WCD wearer's body. The information is used to generate virtual counterparts of the physical wearer's body. Alternatively, a 3D digital replica of the wearer is captured and objects within augmented files or virtual files can be positioned over the wearer's body whether in digitized, or real life version. To try on different configurations, 3D and/or 2D virtual representations of the objects can be superimposed, configured, and/or reconfigured. A library of an augmented and virtual reality files and/or an app for a WCD system is made available and only the wearer's parameters need determination upon which selection can be made from the existing library of wearable elements.

To optimize the fit between a wearer's physical body and the wearable, a three-dimensional object processing module assesses a wearer's physical features by, for example, scanning the physical feature such as the wearer's torso circumferences, length, depth, etc. The 3D and/or image data can then be used to update a memory from the initially or subsequently collected feedback. The feedback 612 can come from a wearer, user such as a clinician or a fitting expert, or a database. Initial data dimensions can assist with setting a baseline and creating a profile of the wearer, which then can be updated and continually revisited throughout a wear period. The fit approximation can be derived from using existing and updated data to provide for changes and improve the fit.

As information aggregates and updates during a wear time, machine learning methods can update and provide suggestions on how to further improve the comfort, sensor positioning and accuracy, and overall wearability. For example, embodiments of a wearable device having a datastore or database module in which data from wear time is stored, a machine learning component (including where is it located), a component that transfers the wear time data from the wearable device to the machine learning component to provide suggestions, and a database module that updates as the fitting is updated.

Such process can also be used in training the prospective wearer on fitting, wearing, adjusting, and managing the system and its components through the wear period. If the system is removed, the fitting processes, which can be largely self-assist process can be important in understanding and reattaching and wearing of the system properly over correct body parts.

Fitting of wearable medical or health systems using a fitting assistant can, in some cases, utilize information regarding internal anatomy and/or physiology, including internal organ imaging and/or internal/external body landmarking for proper placement of elements of a monitoring and/or treatment devices. In some cases, such systems may also utilize information regarding internal anatomy and physiology including internal body imaging and/or internal or external body landmarking.

As indicated in FIG. 6, in a further embodiment, using information or data sets provided during the fitting process, dimension and physiologic mapping determining, session, a virtual reality fitting aspect of this disclosure can create an avatar and use the avatar to outfit a person with a wearable system. The virtual aspect of the fitting assistant application can utilize anatomical and physiologic data, including the augmented fitting data, to create an avatar that is a virtual anatomical and physiologic 3D replica of the patient/wearer/user. Given the 3D image, the assistant can then provide recommendations either visually or verbally, or both, using the device catalog as to the selection of a device and size, given the wearer's needs, as well as the optimal placement around the person's body. Using an application, an avatar of a wearer can be created, or an image of the wearer used, as well as virtual representation of the wearable system and its components, or their images. The system and its components are displayed on the avatar's body as they would be on the wearer. That is, a wearable system can be overlaid onto the avatar. In addition, the virtual wearable system can then be overlaid onto the physical person, using the augmented reality aspect of the application. The system's components can be added or removed in a similar way.

Figure 7:
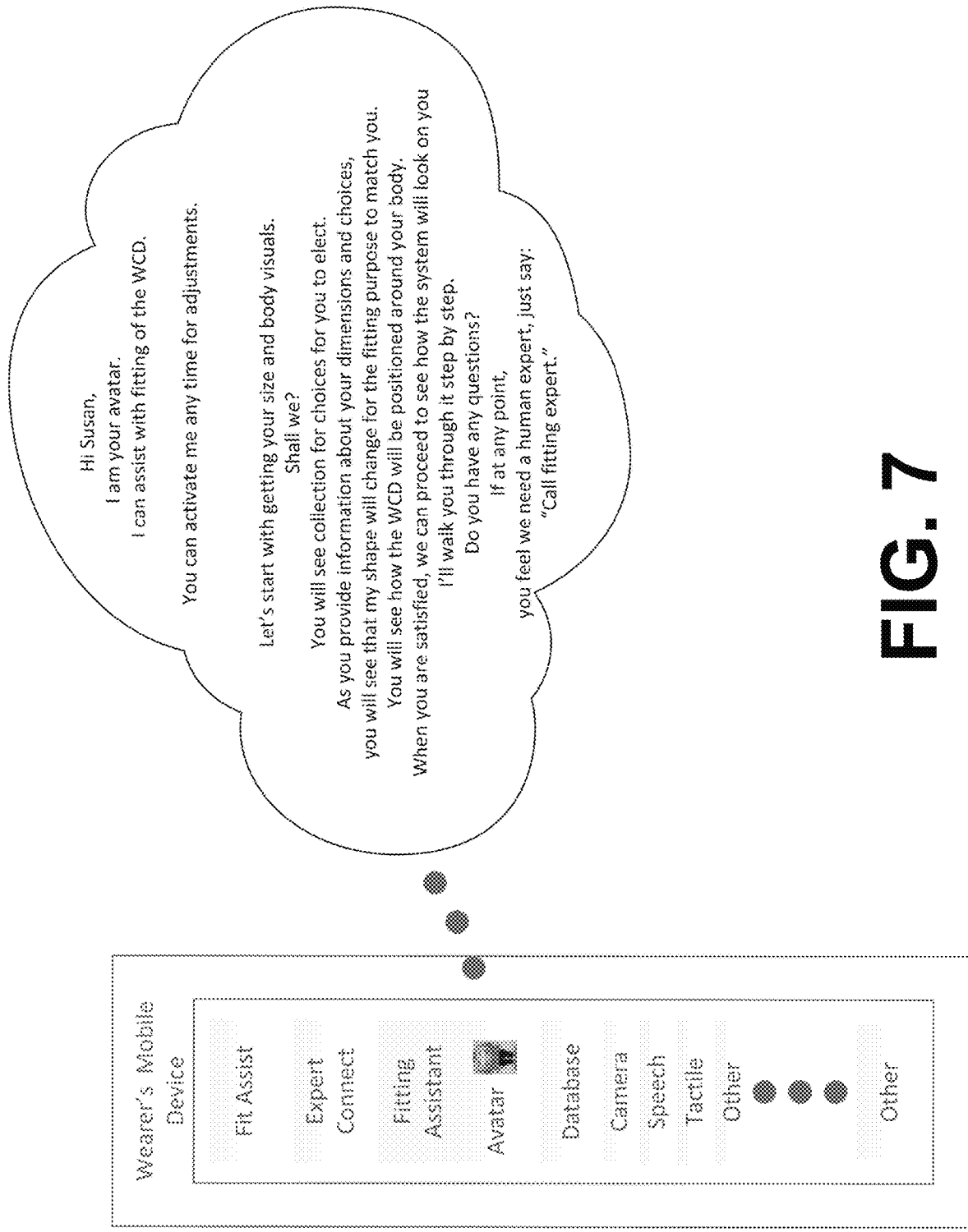
FIG. 7 is a diagram showing a sample image that can be displayed by a fit assist device, such as a mobile communication device, or a headwear device, shown in FIG. 1, in accordance with embodiments.

In a further embodiment, as generally depicted in FIG. 7, an avatar is constructed and can be 2D or 3D, static or dynamic/animated replica of the wearer. The avatar can have other interactive features and in a further embodiment, can be used as a guide for the wearer and/or caregiver. For example, the avatar can walk a patient through the steps of fitting and putting the wearable on, removing, washing the wearable, reapplying of the wearable after it was removed, etc.

A 3D avatar, for example, can be used for the wearer to virtually try on the wearable system, different kinds of systems or modules, and interact with it, view it from different angles, manipulate different elements/components, or expose it to the wearer's activities, different attire overlaying the wearable, and/or movements. The avatar can then illustrate any aspects of the wearer-wearable interaction that should be modified or changed, whether it is that a particular module of the wearable should be swapped for another or instructions to the wearer as to how certain actions may affect wearability, recommendations of different setting depending on the attire or activity, functionality and comfort. The avatar can be used to illustrate if the wearable is too tight, too loose, just right, and also alert of any changes to the wearer's body size or shape.

The fitting assistant app can assist with putting the wearable on, proper placement, and/or repositioning of the wearable's support structure, such as a garment or scaffold for wearable device/element attachment, and optionally also the attachable elements, such as therapy electrodes, monitor/defibrillator, sensor, etc. The app can utilize virtual, augmented, and/or mixed reality capabilities to create an experience of familiarizing the wearer with the WCD, fitting, etc. An avatar can be created, as further illustrated in FIG. 7, as a digital counterpart to reflect a wearer's physical characteristics, including characteristics that support the wearable system. The app's avatar can also guide a patient and/or caregiver on what not to do and how to take proper care of the WCD. A library of videos and animations can be provided for later retrieval along with pictures and/or videos of the patient and the wearable. In a further embodiment, the fitting assistant app can also be utilized with other devices which can be used to display the AR/VR/MR configurations and angles of appearance of the wearable on a wearer.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A Wearable Cardioverter Defibrillator (WCD) system, comprising:
   a support structure configured to be worn on a body of a wearer;
   an electrocardiogram (ECG) electrode configured to be coupled to the support structure, the ECG electrode configured to be positioned on and/or over the body of the wearer;
   a defibrillation electrode configured to be coupled to the support structure, the defibrillation electrode configured to be positioned on and/or over the body of the wearer;
   an external wearable cardioverter defibrillator configured to discharge energy via the defibrillation electrode based at least part on an ECG signal received via the ECG electrode; and
   an augmented reality fit assist device comprising a user interface configured to:
      obtain a position of an internal organ from a database,
      determine a target position for the ECG electrode on the support structure based on a history of attire worn by the wearer and the position of the internal organ of the wearer, and
      display an image of the support structure and indicate the target position for the ECG electrode on the support structure by superimposing a virtual counterpart of the ECG electrode over the image of the support structure.

2. The WCD system of claim 1, wherein the augmented reality fit assist device comprises a processor configured to execute an augmented reality fitting assistant application.

3. The WCD system of claim 2, wherein the augmented reality fitting assistant application is configured to provide a prompt for adjusting the support structure to position the virtual counterpart at the indicated target.

4. The WCD system of claim 3, wherein the prompt comprises a prompt for the wearer to adjust the support structure to adjust a current position of ECG electrode to position the ECG electrode at the indicated target.

5. The WCD system of claim 2, wherein the augmented reality fit assist device comprises a camera.

6. The WCD system of claim 1, wherein the position of the internal organ may be based, at least in part, on an internal organ imaging of the wearer.

7. The WCD system of claim 6, wherein the augmented reality fit assist device is further configured to use one or more features of the support structure as one or more points of reference to determine a dimension of the support structure.

8. The WCD system of claim 1, wherein the augmented reality fit assist device is further configured to receive a user input via the user interface to cause the augmented reality fit device to manipulate the virtual counterpart of the ECG electrode over the image of the support structure.

9. An augmented reality system configured to optimize fitting of a wearable cardioverter defibrillator (WCD) to a body of a wearer, the augmented reality system comprising:
a support structure;
one or more wearable cardioverter defibrillator (WCD) elements; and
an augmented reality fit assist device comprising:
at least one processor configured to execute a fitting assistant application,
at least one sensor configured to obtain digital information about one or more physical features of the body of the wearer of the WCD, and
a user interface configured to:
display one or more augmented reality counterparts of the one or more WCD elements superimposed over a representation of the one or more physical features of the body of the wearer of the WCD, and
further display at least one recommended placement of the one or more augmented reality counterparts of the one or more WCD elements over the representation of the one or more physical features of the body of the wearer of the WCD, the at least one recommended placement based, at least in part, on a position of an internal organ of the wearer and a history of attire worn by the wearer.

10. The augmented reality system of claim 9, wherein the at least one sensor comprises at least one camera.

11. The augmented reality system of claim 10, wherein the fitting assistant application is configured to use one or more features of the support structure as one or more points of reference.

12. The augmented reality system of claim 11, wherein the fitting assistant application is further configured to determine a dimension of the support structure using the one or more points of reference.

13. The augmented reality system of claim 9, wherein the at least one processor is further configured to process information from one or more of an augmented reality database, a virtual reality database, and a database of the wearer.

14. The augmented reality system of claim 9, wherein the at least one processor is further configured to receive a user input via the user interface to cause the at least one processor to manipulate the one or more augmented reality counterparts of the one or more WCD elements over the representation of the one or more physical features of the body of the wearer of the WCD.

15. The augmented reality system of claim 9, wherein the representation of the one or more physical features of the body of the wearer of the WCD is included on an avatar of the wearer.

16. The augmented reality system of claim 15, wherein the avatar comprises at least one of a static or animated avatar and the user interface provides an output comprising a visual feedback, or a tactile feedback, or an auditory feedback, or a combination thereof.

17. The augmented reality system of claim 9, wherein the at least one processor is further configured to receive a user input via the user interface to cause the at least one processor to manipulate the one or more augmented reality counterparts of the one or more WCD elements over a representation of the support structure.

18. The augmented reality system of claim 9, wherein the augmented reality fitting assist application is further configured to provide a prompt for adjusting the support structure to position the one or more augmented reality counterparts at the at least one recommended placement.

19. The augmented reality system of claim 9, wherein the augmented reality fitting assist application is further configured to provide a prompt for adjusting the support structure to position the one or more WCD elements at the at least one recommended placement.

20. The augmented reality system of claim 9, wherein the position of the internal organ is based, at least in part, on an internal organ imaging of the wearer.

* * * * *